United States Patent
Sawada

(10) Patent No.: US 9,829,467 B2
(45) Date of Patent: Nov. 28, 2017

(54) METHOD OF ANALYSIS OF COMPONENT IN SAMPLE, METHOD OF SPECIFIC ISOLATION OF COMPONENT IN SAMPLE, AND SAMPLE FOR MASS SPECTROMETRY

(71) Applicant: National University Corporation Nagoya University, Aichi (JP)

(72) Inventor: Makoto Sawada, Aichi (JP)

(73) Assignee: National University Corporation Nagoya University, Aichi (JP)

( * ) Notice: Subject to any disclaimer, the term of this patent is extended or adjusted under 35 U.S.C. 154(b) by 0 days.

(21) Appl. No.: 15/311,556

(22) PCT Filed: May 12, 2015

(86) PCT No.: PCT/JP2015/063621
§ 371 (c)(1),
(2) Date: Nov. 16, 2016

(87) PCT Pub. No.: WO2015/178249
PCT Pub. Date: Nov. 26, 2015

(65) Prior Publication Data
US 2017/0082579 A1     Mar. 23, 2017

(30) Foreign Application Priority Data

May 19, 2014 (JP) ................................. 2014-103194

(51) Int. Cl.
*G01N 1/28* (2006.01)
*G01N 21/75* (2006.01)
(Continued)

(52) U.S. Cl.
CPC ............. *G01N 27/64* (2013.01); *G01N 27/62* (2013.01); *H01J 49/164* (2013.01); *G01N 2223/612* (2013.01)

(58) Field of Classification Search
USPC ............ 250/281, 282, 288, 423 R, 424, 425; 436/173, 174
See application file for complete search history.

(56) References Cited

U.S. PATENT DOCUMENTS 6,555,813 B1 * 4/2003 Beecher ................ B01L 3/5085
250/281
6,602,661 B1   8/2003 Knezevic et al.
(Continued)

FOREIGN PATENT DOCUMENTS

JP    2002-543440 A    12/2002
JP    2003-505694 A     2/2003
(Continued)

OTHER PUBLICATIONS

Suzuki, H. et al., "Detection of Aβ1-40 monomer/polymers on mouse brain sections by LMD-based MS imaging", Japanese Society for Molecular Imaging Report dated May 15, 2014, p. 169.
(Continued)

*Primary Examiner* — Bernard Souw
(74) *Attorney, Agent, or Firm* — McDermott Will & Emery LLP

(57) ABSTRACT

A trace component in a sample is quickly and accurately analyzed using a small sample quantity without performing preprocessing such as concentration.
Trace components in a sample can be analyzed quickly and accurately using a small sample quantity and without preprocessing such as concentration, by a method for analyzing a component in a sample, the method including a step for irradiating a thermoplastic resin film internally containing the sample with ionizing laser light of a mass spectrometer.

20 Claims, 7 Drawing Sheets

(51) Int. Cl.
*H01J 49/26* (2006.01)
*H01J 49/00* (2006.01)
*G01N 27/64* (2006.01)
*G01N 27/62* (2006.01)
*H01J 49/16* (2006.01)

(56) References Cited

U.S. PATENT DOCUMENTS

| | | | | |
|---|---|---|---|---|
| 8,237,114 | B2* | 8/2012 | Okuno | H01J 49/0418 250/281 |
| 2005/0087685 | A1 | 4/2005 | Bouvier et al. | |
| 2010/0075372 | A1 | 3/2010 | Sato et al. | |
| 2010/0216166 | A1* | 8/2010 | Bonner | G01N 33/543 435/7.21 |

FOREIGN PATENT DOCUMENTS

| | | |
|---|---|---|
| JP | 2004-535566 A | 11/2004 |
| JP | 2012-145530 A | 8/2012 |
| JP | 2013-505438 A | 2/2013 |
| JP | 2013-511734 A | 4/2013 |
| WO | 2008038813 A1 | 4/2008 |
| WO | 2011033046 A1 | 3/2011 |
| WO | 2011064225 A1 | 6/2011 |
| WO | 2015/053039 A1 | 4/2015 |

OTHER PUBLICATIONS

Written Opinion of the International Search Authority, issued in PCT/JP2015/063621 dated Aug. 18, 2015.
Jacquet, R. et al., "Analysis of connective tissues by laser capture microdissection and reverse transcriptase-polymerase chain reaction", Analytical Biochemistry, Elsevier, Amsterdam, NL, vol. 337, No. 1, Feb. 1, 2005, pp. 22-34.
Xu, Baogang J. et al., "Direct Analysis of Laser Capture Microdissected Cells by MALDI Mass Spectrometry", Journal of The American Society for Mass Spectrometry, Nov. 2002, vol. 13, No. 11, pp. 1292-1297.
Palmer-Toy et al., "Direct Acquisition of Matrix-Assisted Laser Desorption/Ionization Time-of-Flight Mass Spectra from Laser Capture Microdissected Tissues", Clinical Chemistry, Sep. 2000, vol. 46, No. 9, pp. 1513-1516.
Extended European Search Report dated May 11, 2017, issued in corresponding European Patent Application No. 15796600.3.

* cited by examiner

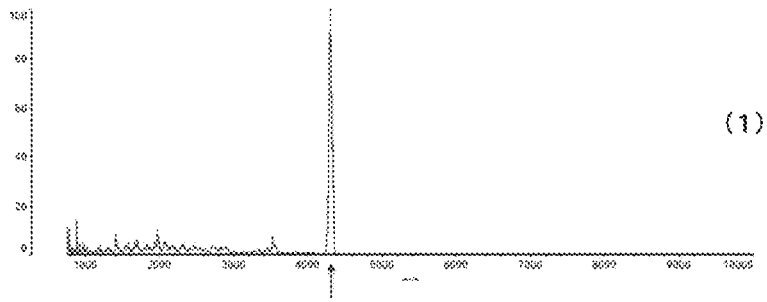
(1)
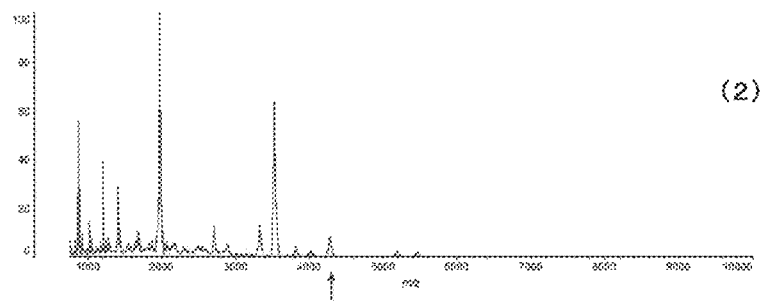
(2)
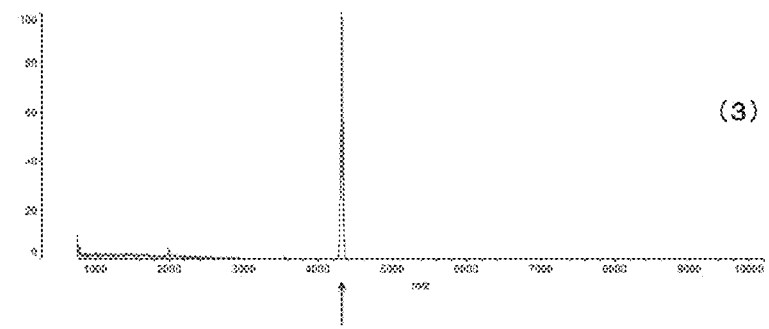
(3)
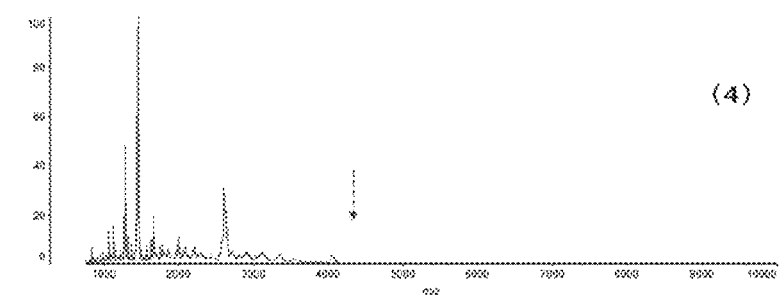
(4)
F I G. 7

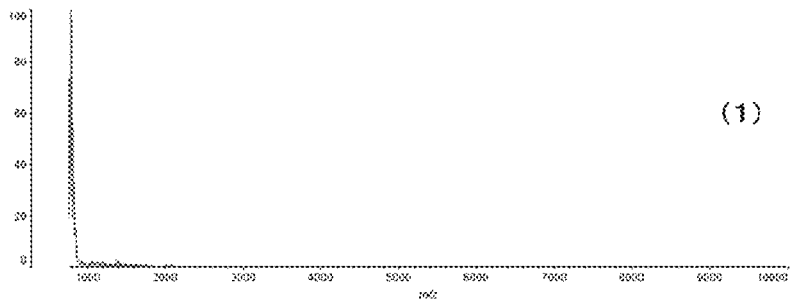
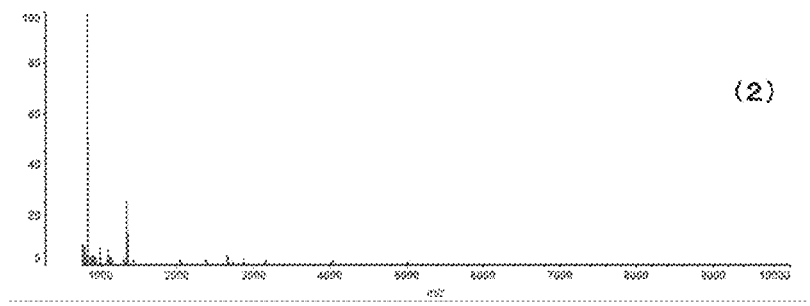
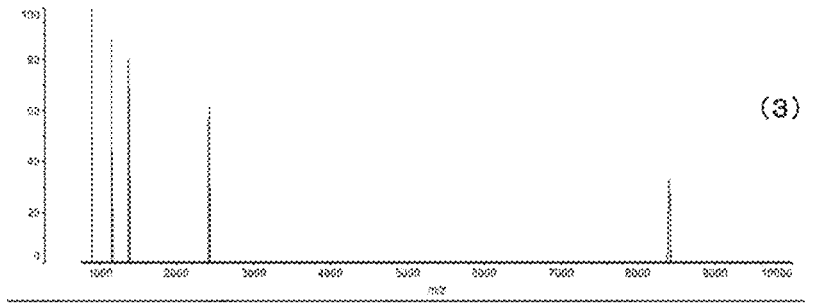
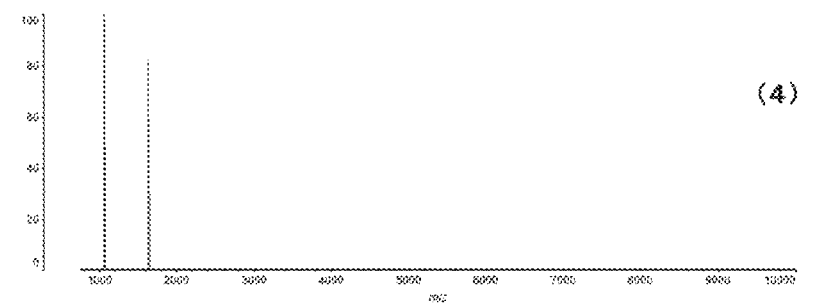
F I G. 8

METHOD OF ANALYSIS OF COMPONENT IN SAMPLE, METHOD OF SPECIFIC ISOLATION OF COMPONENT IN SAMPLE, AND SAMPLE FOR MASS SPECTROMETRY

CROSS-REFERENCE TO RELATED APPLICATION

This application is the U.S. National Phase under 35 U.S.C. §371 of International Patent Application No. PCT/JP2015/063621, filed on May 12, 2015, which in turn claims the benefit and priority from Japanese Patent Application Number 2014-103194, filed May 19, 2014 the subject matters of which are hereby incorporated by reference.

TECHNICAL FIELD

The present application relates to a method for analyzing a component in a sample, a method for specific isolation of a component in a sample, and a sample for mass spectrometry. More specifically, the present application relates to a method in which a molten thermoplastic resin is cooled while being caused to contact a sample, thereby forming a thermoplastic resin film containing the sample, and the thermoplastic resin film is directly irradiated with ionizing laser light of a mass spectrometer, thereby specifically isolating trace components in the sample, without performing concentration or other preprocessing. The present application also relates to a method for analyzing a component in a sample, in which a sample, particularly blood or another biological sample is used, and relates to a sample for mass spectrometry for use in the method of analysis and method of specific isolation.

TECHNICAL BACKGROUND

There has recently been a demand in medical treatment sites for trace components contained in blood, biological tissue, etc., to be analyzed quickly and accurately in small sample quantities.

Proteins, nucleic acids, polysaccharides, etc., are known as biological components contained in blood, biological tissue, etc. These components are analyzed by various methods in accordance with the purpose of medical treatment. For example, peptide hormones in blood are known to participate in various diseases, and by analyzing trace amounts of peptide hormones in blood it is possible to diagnose whether a disease is present.

A common method of analysis of peptide hormones contained in blood involves using antibodies that react specifically with peptide hormones as markers. An example of a known method by which amyloid beta proteins (referred to below as "Aβ"), which are thought to be a cause of Alzheimer's disease, are analyzed from blood is a method involving detection by ELISA using antibodies that specifically recognize Aβ (see, in particular, patent documents 1 and 2).

Methods in which Aβ is analyzed using a mass spectrometer are also known (see, in particular, patent documents 1 and 2).

PRIOR ARTS LIST

[Patent Document 1] JP (Tokuhyo) 2013-505438
[Patent Document 2] JP (Tokuhyo) 2013-511734

SUMMARY OF THE INVENTION

Problems to be Solved by the Invention

However, a problem is presented in the inventions described in the above patent documents 1 and 2 in that various biological components are contained in blood, and since those biological components become impurities when Aβ is detected by ELISA, the detection sensitivity is low. Also, even when blood-borne Aβ is analyzed using a mass spectrometer, a problem is presented in that, typically, the impurities must be removed by immunoprecipitation, etc., to concentrate the Aβ, and the operation is complicated and time-consuming.

Antibody chips are furthermore known as a method of measuring multiple categories of trace analytes simultaneously and inexpensively. However, since it is difficult to arrange antibodies having high specificity and high affinity under the same reaction conditions, it has been difficult to commercialize biological component analysis using antibody chips. As described above, no method is known for analyzing trace components in blood quickly and accurately with a small sample quantity.

The present application was contrived to solve the prior-art problems described above. As a result of thoroughgoing studies, it was discovered that:

(1) a thermoplastic resin film incorporating a sample is formed by irradiating the sample with dissecting laser light of a laser microdissection apparatus to cut out the sample, and cooling while placing the sample in contact with the molten thermoplastic resin;

(2) when the thermoplastic resin film incorporating the sample is irradiated with ionizing laser light of a mass spectrometer, it is not merely that there is an absence of noise originating from the thermoplastic resin film components in the sample, but that the components in the sample can be specifically isolated; and (3) by specific isolation of the sample, trace components, for example, peptide hormones in blood, etc., can be analyzed by mass spectrometry without performing preprocessing such as concentration.

That is, an object of the present application is to provide a method for analyzing a component in a sample, a method for specific isolation of a component in a sample, and a sample for mass spectrometry.

Means to Solve the Problems

The present application relates to a method for analyzing a component in a sample, a method for specific isolation of a component in a sample, and a sample for mass spectrometry, as shown below.

(1) A method for analyzing a component in a sample, the method including a step for irradiating a thermoplastic resin film internally containing the sample with ionizing laser light of a mass spectrometer.

(2) The method of analysis of (1) above, wherein the thermoplastic resin film internally containing the sample is formed by:
a step for heating and melting the thermoplastic resin; and
a step for cooling the molten thermoplastic resin while causing the thermoplastic resin to make contact with the sample.

(3) The method of analysis of (1) or (2) above, wherein the sample is a biological sample.

(4) The method of analysis of (3) above, wherein the biological sample is blood.

(5) The method of analysis of any of (1) to (4) above, wherein the sample, before coming into contact with the molten thermoplastic resin, is dried.
(6) The method of analysis of (5), wherein the sample, before coming into contact with the molten thermoplastic resin, is in a thin film form.
(7) The method of analysis of any of (1) to (6) above, wherein the component in the sample analysed by the method of analysis is a peptide hormone or a lipid.
(8) A method for specific isolation of a component in a sample, the method including a step for irradiating a thermoplastic resin film internally containing the sample with ionizing laser light of a mass spectrometer.
(9) The method of specific isolation of (8) above, wherein the thermoplastic resin film internally containing the sample is formed by:
  a step for heating and melting the thermoplastic resin; and
  a step for cooling the molten thermoplastic resin while causing the thermoplastic resin to make contact with the sample.
(10) The method of specific isolation of (8) or (9) above, wherein the sample is a biological sample.
(11) The method of specific isolation of (10) above, wherein the biological sample is blood.
(12) The method of specific isolation of any of (8) to (11) above, wherein the sample, before coming into contact with the molten thermoplastic resin, is dried.
(13) The method of specific isolation of (12) above, wherein the sample, before coming into contact with the molten thermoplastic resin, is in a thin film form.
(14) A sample for mass spectrometry, the sample including:
  a thermoplastic resin film; and
  a sample laminated on the thermoplastic resin film.
(15) A sample for mass spectrometry, wherein the sample is contained in a thermoplastic resin film.
(16) The sample for mass spectrometry of (14) or (15) above, wherein the sample is a biological sample.
(17) The sample for mass spectrometry of (16) above, wherein the biological sample is blood.

Advantageous Effects of the Invention

In the method for analyzing a component in a sample of the present application, a thermoplastic resin film containing a sample is irradiated with ionizing laser light of a mass spectrometer, whereby impurities in the sample are isolated by the thermoplastic resin film and the component to be analyzed in the sample can be analyzed. Particularly when analyzing trace components such as peptide hormones in blood, using blood, etc., as a sample, the peptide hormones in the blood can be analyzed simply and quickly without performing preprocessing such as antibody-assisted concentration. Accordingly, when, inter alia, diagnosing the onset of Alzheimer's disease, the diagnosis can be performed at the initial stage of the disease onset by detecting the quantity of blood-borne peptide hormones.

Furthermore, in the method for specific isolation of a component in a sample of the present application, a thermoplastic resin film internally containing a sample is irradiated with ionizing laser light of a mass spectrometer, whereby the component in the sample can be specifically isolated by the thermoplastic resin film. Accordingly, the component in the sample can be isolated simply and quickly without performing preprocessing of diverse samples.

Furthermore, the sample for mass spectrometry of the present application can be stored or moved in a state of having been laminated on or contained in a thermoplastic resin film. Accordingly, because the sample can be handled as one body with the thermoplastic resin film, blood or another biological sample extracted at a hospital, etc., lacking a mass spectrometer can be sent to a hospital, analysis center, etc., having a mass spectrometer and readily analyzed.

BRIEF DESCRIPTION OF THE DRAWINGS

FIGS. 7 (1) to (4) illustrate mass spectra obtained in examples 3 to 6;
FIGS. 8 (1) to (4) illustrate mass spectra obtained in examples 7 to 10.

DESCRIPTION OF THE PREFERRED EMBODIMENTS

Figure 1:
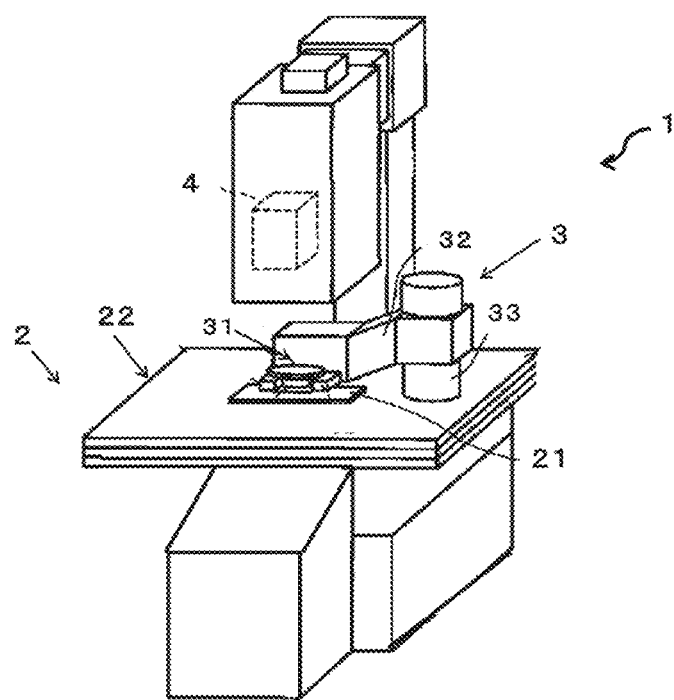
FIG. 1 is a schematic depiction of a laser microdissection apparatus 1.

The method for analyzing a component in a sample, method for specific isolation of a component in a sample, and sample for mass spectrometry of the present application are described in detail below.

First, in the present application, "thermoplastic resin film internally containing a sample" signifies a thermoplastic resin film in which it is not merely that a sample is placed thereon; in a process of melting a thermoplastic resin and then cooling and solidifying same, the thermoplastic resin is mixed with the sample and the sample is incorporated inside the thermoplastic resin formed into a film.

The thermoplastic resin used in the present application is not limited in form and raw material, provided that the resin can be rendered into the form of a film by melting and a sample can be incorporated inside. For example, a sample may be incorporated in the thermoplastic resin film by being placed on a film-form thermoplastic resin, then heating, melting, and subsequently cooling the combination. Also, a thermoplastic resin film internally incorporating a sample may be produced by a process of mixing the sample with a thermoplastic resin particulate, then heating, melting, and subsequently cooling the mixture.

Thermal denaturation of the sample can be prevented in thermoplastic resins having a lower melting point, a thermoplastic resin having a melting point up to about 50° C. to 70° C. is preferably used for the raw material, examples of which include ethyl vinyl acetate (EVA), polyolefins, polyamides, acrylics, and polyurethane. When the sample to be isolated or analyzed has exceptional thermal stability, the temperature may be at or above the aforementioned temperature. Also, as is to be described later, when the sample is cut out by dissecting laser and compounded in the thermoplastic resin film, naphthalene cyanine dye or another organic dye may be added in order to selectively absorb the spectrum in the wavelength region of the dissecting laser light source in the thermoplastic resin, and a suitable organic dye should be selected in accordance with the wavelength region of the dissecting laser light used. The thermoplastic resin may be produced by suitably blending the thermoplastic resin and the organic dye, or a commercially available thermoplastic resin film may be used. Examples of commercially available thermoplastic resin films include thermoplastic transfer films (Electro Seal Ltd.) and thermoplastic EVA films (Sigma-Aldrich Japan).

The sample is not provided by any particular limitation, provided that the sample can be incorporated in the molten thermoplastic resin film and components in the sample can be analyzed by mass spectrometer. Examples of samples include blood, saliva, urine, and other liquid samples, and muscle, bone, brain, organs, and other biological tissues, extracted from living bodies (liquid samples and biological tissues extracted from living bodies are referred to below as "biological samples"), and food, soil, bacteria, and viruses.

Also, the components in the sample are not particularly limited, provided that the components can be analyzed by mass spectrometer. Examples of samples include, in the case of biological samples, $A\beta$, insulin, and other peptide hormones; proteins; neutral lipids, phospholipids, and other lipids; galactose, glucosamine, and other sugars; RNA, DNA, and other amino acids. Also, pathogens, toxins, drugs, or other components can be analyzed from blood, urine, or other liquid samples from victims of food poisoning, drug users, etc. Food additives, vitamins, or other nutritional components, etc., can be analyzed when the sample is food. Residual agrochemicals or other pollutants can be analyzed when the sample is soil. When the sample is bacteria or viruses, the sample can be simply analyzed, without using antibody reactions, etc., by analyzing, for example, toxins contained in O-157 or other bacteria or toxic substances contained in influenza virus, etc.

These samples may contain water provided that the samples can be incorporated in the thermoplastic resin, but the samples may be dried in order to facilitate incorporation. The drying method should be capable of ridding the sample of water, and well-known drying methods should be used, for example, drying inside a container with an internally sealed desiccant, vacuum drying, freeze drying, and alcohol drying. "Drying" in the present application does not signify completely eliminating water in the sample, but signifies reducing the water content of the sample in order to facilitate incorporation of the sample in the thermoplastic resin, and the water content of the sample may be such that the sample can be incorporated in the thermoplastic resin.

The method of production of the sample for mass spectrometry is not particularly limited, provided that the sample can be incorporated in the thermoplastic resin film. For example, when mixing the sample with a thermoplastic resin particulate, the sample should be pulverized by vacuum drying, freeze drying, etc., and mixed with the thermoplastic resin particulate. Also, when using a film-form thermoplastic resin, the sample also should be used in the form of a thin film. The thin film-form sample should be produced by a well-known method. For example, in the case of blood or miso or other viscous food, by placing the sample on a glass slide and pulling another glass slide while applying pressure, a thin film of the sample can be formed on the glass slide, and the formed thin film should be vacuum dried or alcohol dried. Also, in the case of biological tissues, a frozen block can be produced placing the sample in an embedding agent, frozen slices can be produced from the frozen block, and the obtained slices can be vacuum dried, alcohol dried, etc.

Heating of the thermoplastic resin is not particularly limited, provided that the thermoplastic resin can be melted. For example, the sample may be placed on the thermoplastic resin film, and the thermoplastic resin may be melted by being heated on a hot plate; moreover, a pulverulent or thin film-form sample may be mixed with a thermoplastic resin powder and placed on a glass plate, etc., and the thermoplastic resin may be melted by being heated on a hot plate. Because the water content of the sample is reduced during heating when the thermoplastic resin (film) is heated and melted on the hot plate; e.g., blood or another liquid sample may be mixed with the thermoplastic resin, or the liquid sample may be spread thinly on the thermoplastic resin film, and be heated. Also, the sample may be placed on the thermoplastic resin film, the sample may be irradiated with dissecting laser light using a laser microdissection apparatus, the thermoplastic resin can be melted at the same time as the sample is cut out, and the cut-out sample may be incorporated into the thermoplastic resin.

FIG. 1 is a schematic diagram of a laser microdissection apparatus 1, which includes a sample moving means 2, a thermoplastic resin film moving means 3, a laser irradiation unit 4, a memory means, and a moving means drive control unit (not shown).

The sample moving means 2 illustrated in FIG. 1 includes: a sample mounting stand 22 on which is mounted a glass slide 21 that has a sample mounted thereon; a drive source (not shown) for moving the sample mounting stand 22 in a horizontal direction (X or Y axis direction); and a drive power transmission mechanism for transmitting drive power of the drive source to the sample mounting stand 22. A pulse motor, ultrasonic motor, etc., may be used as the drive source. Also, the drive power transmission mechanism may be a well-known drive power transmission mechanism; e.g., one for driving a sample mounting stand used on an inverted microscope, etc., in a horizontal direction.

The thermoplastic resin film moving means 3 illustrated in FIG. 1 includes: an arm 32 having one end capable of mounting a thermoplastic resin film 31 and having another end that can be attached on an arm support 33; an arm support 33 capable of rotating the arm 32 in a horizontal direction (X or Y axis direction) and moving the arm 32 in a vertical direction (Z axis direction); a drive source (not shown) for rotating the arm 32 in the horizontal direction and moving the arm in the vertical direction; and a drive power transmission mechanism for transmitting drive power of the drive source to rotate and move the arm 32. A pulse motor, ultrasonic motor, etc., may be used as the drive source. Also, the drive power transmission mechanism may be, for example, an arm mechanism for moving a sample on an automatic analyzer, or other well-known arm mechanism capable of rotating in the horizontal direction and moving in the vertical direction. The thermoplastic resin film moving means 3 is not limited to the embodiment illustrated in FIG. 1, and there is no limitation in particular, provided that the thermoplastic resin film 31 can be moved in the horizontal direction and vertical direction.

The dissecting laser light source preferably employs single-mode output laser light in order to minimize the irradiation spot. Also, a near-infrared high-NA length, long-focus objective lens for light collection is preferably used. Also, the light source preferably generates pulse laser light having a pulse width of 0.1 milliseconds to 100 milliseconds, preferably 5 milliseconds, having a wavelength of 785 nanometers to 900 nanometers, preferably 808 nanometers, having an output of 0.2 to 0.3 W, and having an irradiating laser power of 0.1% to 100%, preferably 80% to 100%. A specific example is Z-808-200-SM (Lucille Co.).

Figure 2:
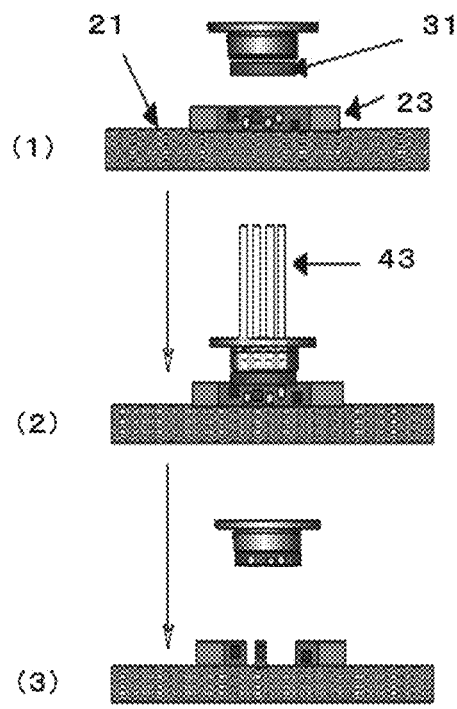
FIGS. 2 (1) to (3) are diagrams illustrating one example of the principle of production of a thermoplastic resin film internally containing a sample, using a laser microdissection apparatus.

FIG. 2 are diagrams illustrating one example of the principle of production of a thermoplastic resin film internally containing a sample, using the laser microdissection apparatus. As illustrated in FIG. 2(1), a sample 23 fixed to a glass slide 21 and a support body of optically transparent acrylic resin, polycarbonate resin, or other resin having a thermoplastic resin film 31 attached thereto are prepared. Next, as illustrated in FIG. 2(2), the thermoplastic resin film 31 is placed in contact with the sample 23, and the sample 23 is irradiated with dissecting laser light 43 through the support body and the thermoplastic resin film 31. Next, as illustrated in FIG. 2(3), the thermoplastic resin film 31 is peeled from the sample 23, at which time the sample 23 cut out by being irradiated with the dissecting laser light 43 is separated to be contained inside the thermoplastic resin film 31 melted by being irradiated with the dissecting laser light 32, and the molten thermoplastic resin film solidifies, whereby the thermoplastic resin film internally containing the sample can be produced.

The present application is characterized by specifically isolating a component in a sample using a thermoplastic resin film and analyzing the isolated component in mass spectrometry. Therefore, for example, when analyzing a trace component in blood, there is no need to specify the portion of the thin film sample produced from blood where the component to be analyzed is contained, and therefore the desired location of the thin film sample should be irradiated with dissecting laser light as illustrated in FIG. 2.

Figure 3:
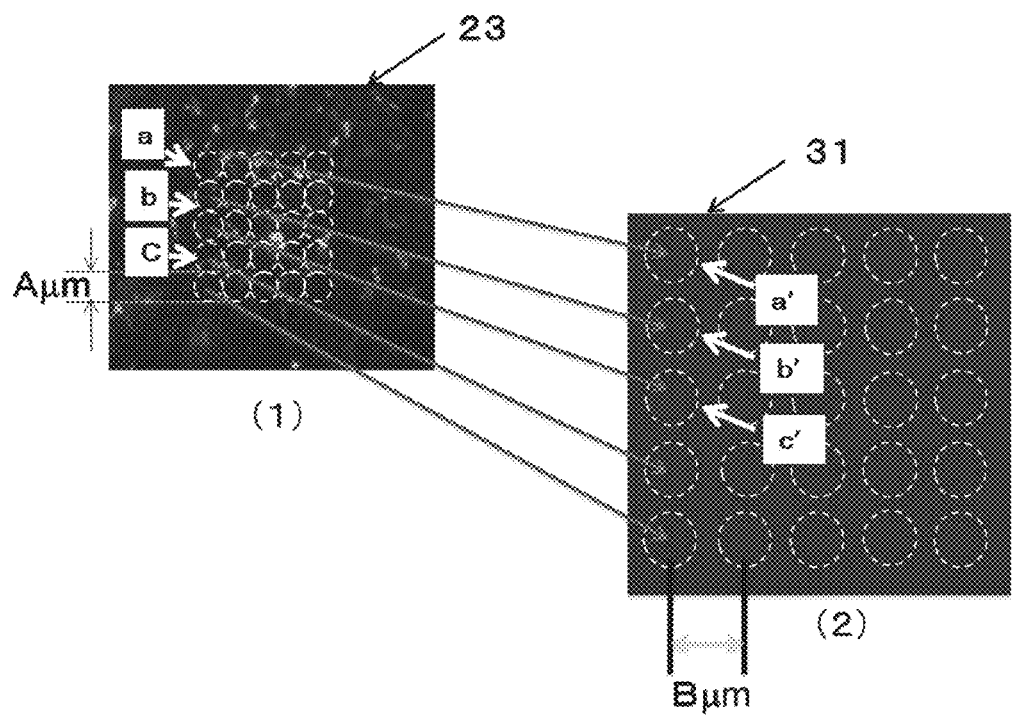
FIGS. 3 (1) and (2) are diagrams representing the relationship between the positional coordinates of a sample in the location of irradiation with dissecting laser light and the positional coordinates of a thermoplastic resin film incorporating the cut-out sample.

Meanwhile, when specifically isolating and analyzing biological components in specific regions of frozen slices of brain, organs, or other biological tissues, the interval of cut-out samples and the interval of thermoplastic resin films incorporating the samples may be changed in order to improve spatial resolution. FIG. 3 are diagrams representing the relationship between the positional coordinates of a sample in the location of irradiation with dissecting laser light and the positional coordinates of a thermoplastic resin film 31 incorporating the cut-out sample, and the case in which samples are successively cut out is illustrated. For example, when successively cutting out samples 23 in FIG. 3(1) as a, b, c, . . . , (i) part a of the samples 23 is moved by the sample moving means 2 to the position to be irradiated with dissecting laser light. (ii) Next, the location a' in the thermoplastic resin film 31 illustrated in FIG. 3(2) where the cut-out sample a is be incorporated is moved by the thermoplastic resin film moving means 3 to a position overlapping with the sample 23a, and the sample 23 is placed in contact with the thermoplastic resin film 31 by lowering the arm 32 in the vertical direction. (iii) Irradiation with laser light is performed, whereby the sample cut out from the location of the sample 23a is adhered to the position of a' on the thermoplastic resin film 31; next, the arm 32 is raised in the vertical direction whereby the thermoplastic resin film 31 is removed from the sample 23, and the sample 23a is incorporated in the predetermined location of the thermoplastic resin film 31. The samples 23b, c, . . . can be incorporated in b', c', . . . of the thermoplastic resin film 31 by repeating the procedures in (i) to (iii) for samples 23b, c, . . . .

The size A of the sample to be extracted from the sample 23 should be changed as the size of the target sample or of the sample to be cut out in accordance with the purpose. For example, a sample having a size of 1 to 5 μm in the case of analysis of subcellular structures or wanting to obtain high spatial resolution, 15 μm to 30 μm in the case of extracting single cells, or 50 μm to 100 μm in the case of extracting cancers or mutated sites should be cut out and extracted from the sample 23 by irradiation with dissecting laser light. The size of the sample to be cut out can be the result of cutting out a sample having the same size as the diameter of the dissecting laser light by adjusting the diameter and intensity of the irradiating dissecting laser light, and can be the result of cutting out a sample being larger than the diameter of the dissecting laser light by increasing the intensity of the dissecting laser light or lengthening the time of irradiation. The diameter and intensity of the dissecting laser light should be adjusted in accordance with the sample to be extracted. The diameter of the dissecting laser light should be obtained by adjusting the focus using an optical aperture, collection lens, etc. The intensity of the dissecting laser light should be obtained by changing the voltage of the laser oscillator body using a variable resistor, etc.

Furthermore, when performing two-dimensional and three-dimensional mass imaging on the basis of analytical results of the sample, the image processing should be performed associating the positional coordinates of the cut-out sample, the positional coordinates of the thermoplastic resin film incorporating the cut-out sample, and the positional coordinates of the analyzed sample with the analytical results. The mass imaging can be performed inexpensively using a conventional mass spectrometer by associating the positional coordinates with the analytical results.

In the method for analyzing a component in a sample and method for specific isolation of a component in a sample of the present application, it is believed that the components in the sample and the thermoplastic resin film interact somehow when being irradiated with ionizing laser light of the mass spectrometer, and a difference appears in the flight of the ionized components as a result. Accordingly, the components to be analyzed can be analyzed by suitably setting the combination of the kind of thermoplastic resin and the sample to be analyzed (or components to be analyzed). As mentioned above, in the present application, it is believed that a difference appears in the flight of the ionized components by an interaction between the components in the sample and the thermoplastic resin film. Therefore, it is believed that the sample and the thermoplastic resin film undergo some kind of interaction on adhesive surface of the sample and the thermoplastic resin film, even without heating and melting the thermoplastic resin film in advance. For example, when the sample is very thin, or when the components to be analyzed in the sample are many, it is believed that the components in the sample can be analyzed even by performing mass spectrometry with the sample being laminated on the thermoplastic resin film. The mass data obtained by the analysis may differ from the analytical values with pure substances because the initial speed varies by the thickness of the thermoplastic resin film.

The mass spectrometer used in the present application is not particularly limited, provided that a biological sample is ionized by irradiating with ionizing laser light and the ions are analyzed; examples including matrix-assisted laser-desorption/ionization time-of-flight mass spectrometer (MALDI-TOF-MS) and high-performance liquid chromatograph/mass spectrometer (LC-MS).

Because the sample for mass spectrometry of the present application should be incorporated in a thermoplastic resin film when irradiating with ionizing laser light of a mass spectrometer, the sample may be stored and sent in a state being laminated on the thermoplastic resin, or the thermoplastic resin film may be heated and melted and the sample may be incorporated inside in advance of mass spectrometry. Also, the sample may be stored and sent in a state being incorporated in the thermoplastic resin film. Accordingly, because the extracted sample can be handled as one body with the thermoplastic resin film, a sample extracted at a hospital, etc., lacking a mass spectrometer can be sent to a hospital, analysis center, etc., having a mass spectrometer and can be analyzed simply. Also, the sample for mass spectrometry of the present application may include at least a thermoplastic resin and a sample, but a glass slide, etc., may also be included as needed.

The present application is described specifically with examples below, but the examples are merely for the purpose of describing the present application and therefore are provided for the purpose of reference to embodiments. These illustrations are given for the purpose of illustrating specific embodiments of the present application, but do not represent any limitation or restriction of the scope of the application disclosed in the present specification.

EXAMPLES

Production of Sample for Mass Spectrometry

Example 1

Production of Blood Sample

A blood sample was produced by adding Aβ 1-40 peptide (Peptide Institute, Inc.) to a concentration of 10 nM to 100 μl of blood extracted from a mouse (B57BL6, Charles River Laboratories).

(Production of Laser Microdissection Apparatus)

A laser microdissection apparatus was produced based on an inverted microscope (Olympus IX series), attaching a stepping motor (BioPrecision; produce of Rudoru Co.) as a drive source, 3D-A-LCS software (produce of Lucille Co.) as a moving means drive control unit, and Z-808-200-SM (produce of Lucille Co.) as a dissecting laser light source.

(Incorporation of Blood Sample into Thermoplastic Resin)

Figure 4:
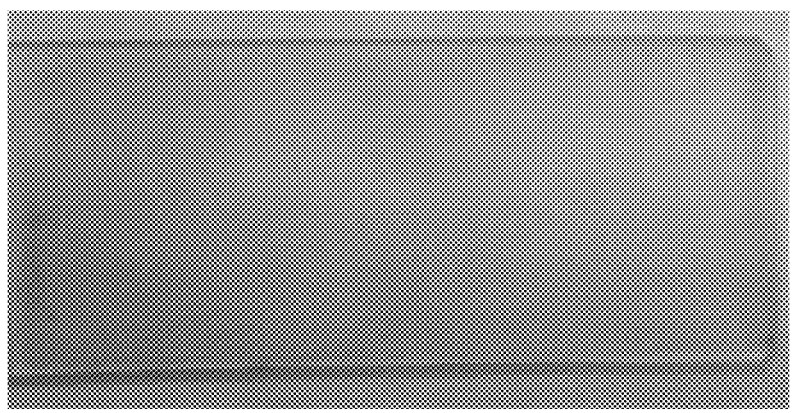
FIG. 4 is a photograph, used instead of a diagram, of a thin film of a blood sample.

5 μl of the above blood sample was dripped on a 26 mm×76 mm glass slide, and a smear of blood uniformly smeared on the glass slide was produced by pressing and moving a glass slide of the same size. Next, the glass slide smeared with blood was immersed in 70% ethanol for 1 minute→100% ethanol for 1 minute→100% ethanol for 1 minute, 100% xylene for 1 minute→100% xylene for one minute, and dried, and a thin film of the blood sample was produced. FIG. 4 is a photograph of the thin film of the blood sample. Next, the thin film of the blood sample was incorporated in a thermoplastic resin film by the procedure below.

(1) After turning on the power of the laser microdissection apparatus and initializing the sample mounting stand, the obtained thin film of the blood sample was set on the sample mounting stand of the laser microdissection apparatus. Also, a hollow ring having an EVA film (produce of Sigma-Aldrich Japan) attached on the leading end was inserted into a hole on the leading end of the arm of the thermoplastic resin film moving means.

(2) The thin film of the blood sample fixed on the glass slide was irradiated with dissecting laser light (output: 300 mA, irradiation time: 5 msec, irradiation diameter: 30 μm) in accordance with the Live Cell Imaging System V7 (product of Lucille Co.) program, and the cut-out blood sample was incorporated inside the EVA film, whereby the sample for mass spectrometry was produced.

Comparative Example 1

A sample for mass spectrometry not including an EVA film was produced by producing a thin film of a blood sample by the same procedure as in example 1 on an electrically conductive glass slide (Sigma-Aldrich Corporation, Cat. No. 578274, Indium tin oxide coated glass slide).

Mass Spectrometry of Produced Sample

Example 2

The sample for mass spectrometry produced in example 1 was subjected to mass spectrometry by the procedure below.

(1) The sample for mass spectrometry was affixed to electrically conductive double-sided tape with the surface including the blood sample facing up.

(2) A matrix for supplying to MALDI-TOF-MS was applied by chemical printer on the surface of the sample for mass spectrometry. CHCA (50% acetonitrile, 0.1% TFA) was used for the matrix, and a quantity of 10,000 pl (100 pl×5 drops/1 spot×20 times) was applied.

(3) Angiotensin 2 (M.W. 1046.3) and Insulin (M.W. 5804.6) were used in a blunt carrier, and the positional information of the blunt carrier was set.

Figure 5:
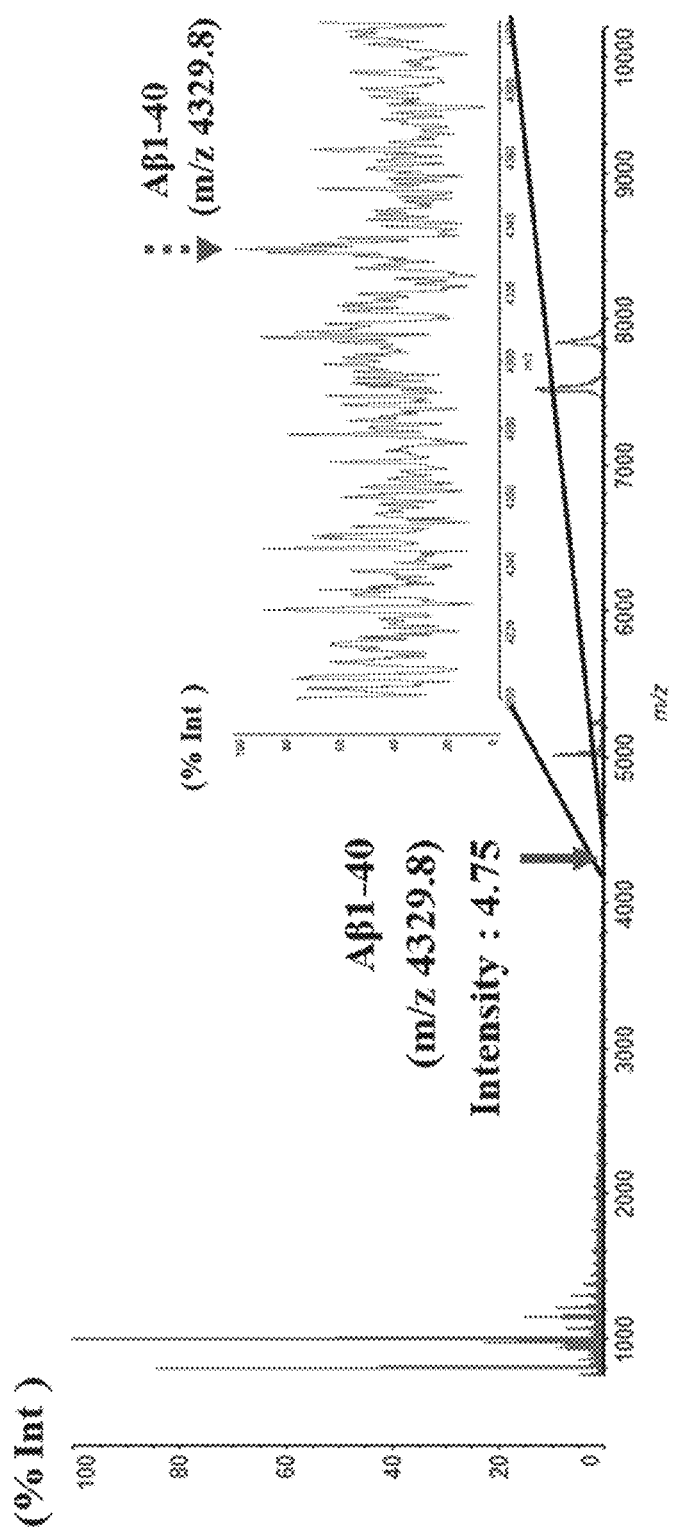
FIG. 5 illustrates a mass spectrum obtained in example 2.

(4) The EVA film was moved to a desiccator and was dried for 20 minutes with a vacuum pump, and then was subjected to mass spectrometry by AXIMA Performance (Shimadzu Corporation). The measurement conditions of the mass spectrometry were Laser Power 65, Profile 1, Shots 200, and each parameter was set in a ChIP Imaging Experiment. FIG. 5 illustrates the mass spectrum as the analytical result by AXIMA Performance.

Comparative Example 2

Figure 6:
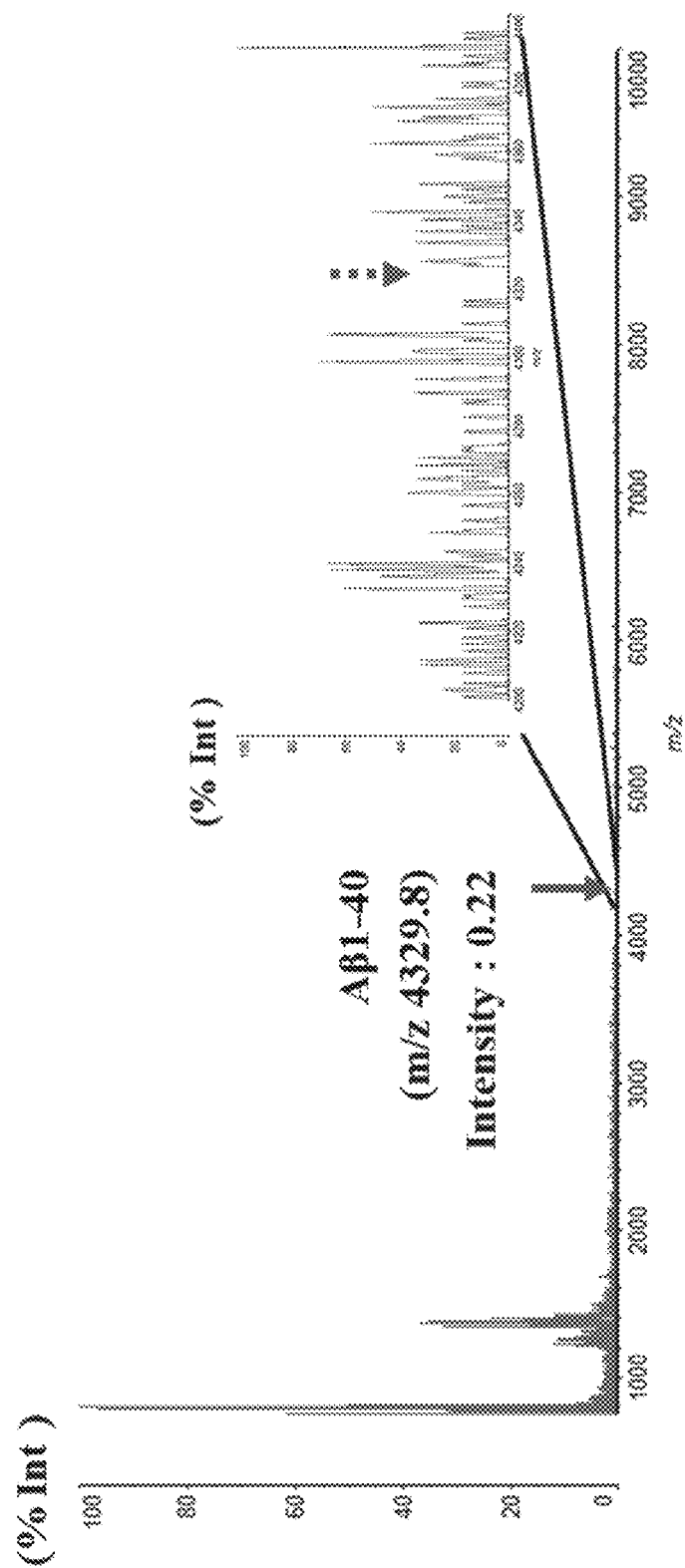
FIG. 6 illustrates a mass spectrum obtained in comparative example 2.

Mass spectrometry of a produced sample was performed by the same procedure as in example 2, except that the sample for mass spectrometry produced in comparative example 1 was used. FIG. 6 illustrates the obtained mass spectrum.

As is clear from FIGS. 5 and 6, between the case when the blood sample incorporated in the EVA film of example 2 was irradiated by ionizing laser and the case when the blood sample of comparative example 2 was directly irradiated by ionizing laser, the peak at 800 to 1400 m/z is smaller and the peak near 1600 to 4000 m/z is comparatively smoother for example 2. This is inferred to be because components that are difficult to ionize and components that are easily ionized in the blood sample are specifically isolated by the EVA film by incorporating the blood sample in the EVA film, compared with the case when the blood sample was directly ionized. Also, when enlarging the peak near 4329.8 m/z (solid-line arrow in FIGS. 5 and 6), being the peak of Aβ, the peak of Aβ could not be confirmed in comparative example 2 (dotted-line arrow), but the peak of Aβ (dotted-line arrow) was confirmed in example 2. By the fact that the components (impurities) that are difficult to ionize in the blood sample were isolated by the EVA film, it became clear that the sensitivity of analysis is improved and even trace amounts of Aβ can be analyzed. This sensitivity is at least 20 times or higher from the viewpoint of FIGS. 5 and 6, and analysis of Aβ can be performed quickly from a minute blood sample by the present invention.

Experiment with Different Kinds of Thermoplastic Resin

Example 3

Adjustment of Blood Sample

A blood sample was produced by the same procedure as in example 1, except that the Aβ 1-40 peptide was added to a concentration of 1 μm.

(Incorporation of Blood Sample into Thermoplastic Resin)

A polyacrylic resin film (joint-stock company Moribe Shoten, FA-1150) was placed on top of an electrically conductive glass slide (Sigma-Aldrich Corporation, Cat. No. 578274, Indium tin oxide coated glass slide). Next, 5 μl of the above blood sample was dripped on the polyacrylic resin film, and the sample was heated for 5 minutes at 100° C. using a hot plate (product of As One Corporation, PC-420D) and was next cooled at room temperature. After fully cooling, the sample was dried overnight in a desiccator filled with silica gel, whereby the polyacrylic resin film incorporating the blood sample was produced, and mass spectrometry was performed by the same procedure as in example 2. FIG. 7(1) illustrates the mass spectrum obtained in example 3.

Example 4

Mass spectrometry was performed in the same manner as in example 3, except that a polyolefin resin film (joint-stock company Moribe Shoten, FA-3050) was used. FIG. 7(2) illustrates the mass spectrum obtained in example 4.

Example 5

Mass spectrometry was performed in the same manner as in example 3, except that a polyester resin film (joint-stock company Moribe Shoten, FA-4100) was used. FIG. 7(3) illustrates the mass spectrum obtained in example 5.

Example 6

Mass spectrometry was performed in the same manner as in example 3, except that a polyurethane resin film (joint-stock company Moribe Shoten, FA-7300) was used. FIG. 7(4) illustrates the mass spectrum obtained in example 6.

As is clear from FIGS. 7(1) to (4), the Aβ was detected with high sensitivity when a polyacrylic resin and a polyester resin were used, but the sensitivity was low when a polyolefin resin was used, and the Aβ was not detected when a polyurethane resin was used. It became clear from the above results that the kind of thermoplastic resin film desirably should be adjusted suitably in accordance with the component to be analyzed.

A mass spectrometric spectrum is expressed by relative value with the maximum peak as 100. Therefore, in the results of mass spectrometric spectra in the above examples 3 to 6, because the heights of the spectra of the components contained in the blood differ greatly according to the sensitivity of detection of Aβ, it is difficult to understand the specific isolation of the blood components according to the difference in kind of thermoplastic resin. Therefore, the following experiment was carried out using only blood not containing Aβ as a sample.

Examples 7 to 10

Mass spectrometry was performed by the same procedure as in examples 3 to 6, except that only blood not containing Aβ was used as samples, and these were respectively designated as examples 7 to 10. FIG. 8(1) illustrates the mass spectrum of example 7, FIG. 8(2) illustrates the mass spectrum of example 8, FIG. 8(3) illustrates the mass spectrum of example 9, and FIG. 8(4) illustrates the mass spectrum of example 10.

As is clear from FIGS. 8(1) to (4), the characteristics of isolation of the components of the samples themselves differed by varying the kind of thermoplastic resin film. Accordingly, it became clear that the kind of thermoplastic resin film desirably should be adjusted suitably, not only in accordance with the component to be analyzed in the sample, but also in accordance with the sample containing the component to be analyzed.

Analysis of Components Other than Peptides

Example 11

Acquisition of Analytical Tissue

The brain of an APP/PS1 mouse (10 months old, about 25 g) acquired by the procedure below was used as analytical tissue.
1. The mouse was anesthetized with diethyl ether, then placed in a supine position, and the limbs were secured.
2. After laparotomy, the diaphragm was incised, and the lateral ribs were incised toward the head direction.
3. The xiphoid process was squeezed and reversed toward the head direction, and fixed with forceps, and the heart was exposed.
4. A butterfly needle was inserted into the left ventricle, and 1×PBS solution (saline) was injected.
5. The right atrial appendage was incised with scissors, and blood removal and perfusion were carried out with about 70 mL of saline.
6. After perfusion, the head was removed, and after craniotomy, the brain was excised.
7. The excised brain was cut in half on the sagittal section, the cut surface was placed downward (on the cutting surface), then the brain was placed in an embedding agent (OCT compound) and frozen, and a frozen block was thus produced.

(Production of Sample Slice)

A sample slice was produced by the procedure below from the frozen block obtained by the above procedure.
1. A slice was produced having a thickness of 10 μm from the frozen block. A non-coated glass slide was used.
2. The frozen slice was dried by the procedure below.

| | |
|---|---|
| (1) 100% acetone | 10 minutes |
| (2) PBS | 1 minute |
| (3) 70% ethanol | 1 minute |
| (4) 100% ethanol | 1 minute |
| (5) 100% ethanol | 1 minute |
| (6) 100% xylene | 2 minute |
| (7) 100% xylene | 2 minutes |

(Cutting Out of Sample from Slice and Incorporation into Thermoplastic Film)

The obtained frozen slice was cut out using a laser microdissection apparatus by the same procedure as in example 1, and incorporated in an EVA film, and a sample for mass spectrometry was produced.

(Mass Spectrometry of Produced Sample)

Figure 9:
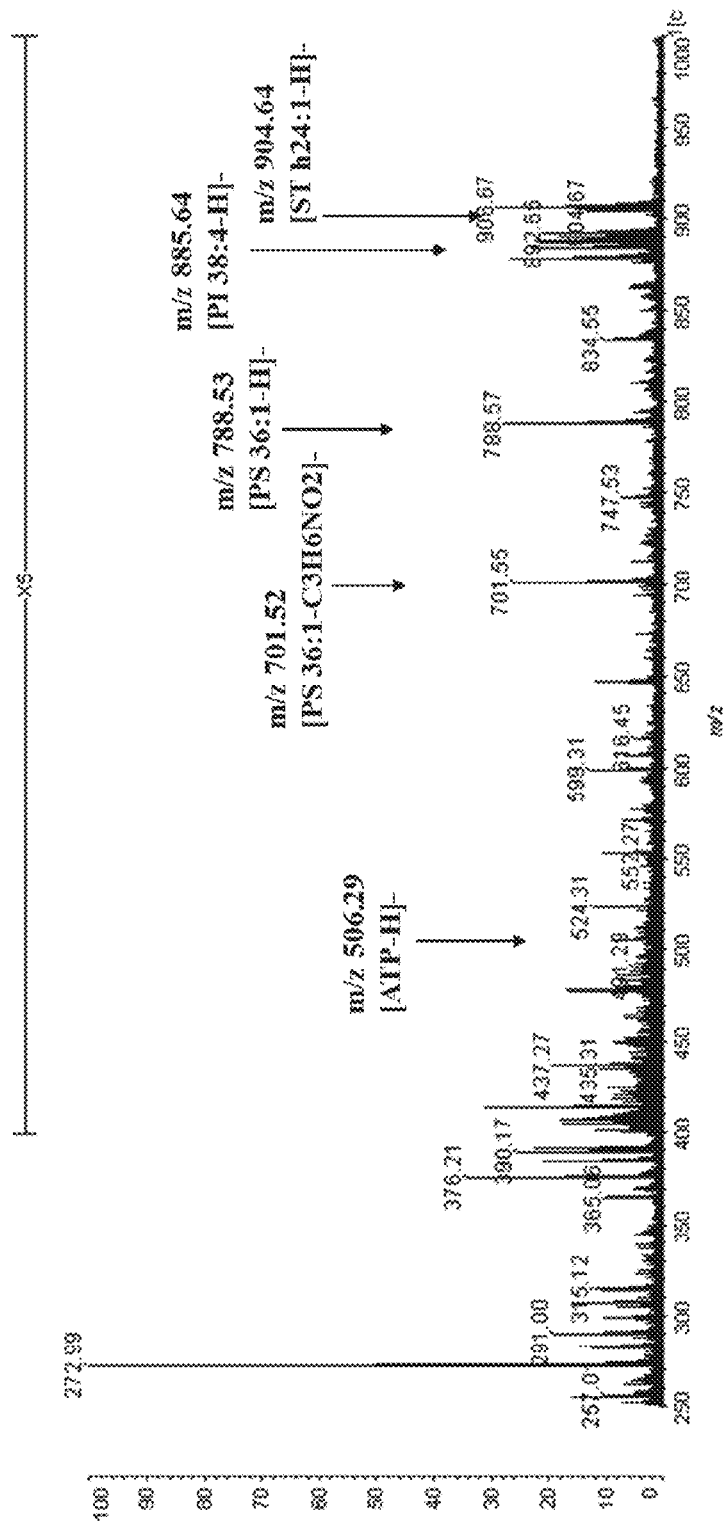
FIG. 9 illustrates a mass spectrum obtained in example 11.

Mass spectrometry was performed in the same manner as in example 2, except that DHB-α-cyano-4-hydroxycinnamic acid (Sigma-Aldrich Corporation) was used for the matrix. FIG. 9 illustrates the mass spectrum obtained in example 11.

As is clear from FIG. 9, when brain, being a biological tissue, was used as a sample, adenosine triphosphate (the arrow at m/z 506.29), phosphatidylserine (the arrow at m/z 701.52 is phosphatidylserine having isolated $C_3H_6NO_2$ therefrom; the arrow at m/z 788.53 in the drawing is phosphatidylserine having isolated H therefrom), phosphatidylinositol (the arrow at m/z 885.64 in the drawing), sulfatide (the arrow at m/z 904.64 in the drawing), etc., were detected. It was learned that biological components other than peptide hormones also can be analyzed by the present application.

INDUSTRIAL APPLICABILITY

Trace components in various samples can be specifically isolated and analyzed quickly, without performing preprocessing such as concentration, by using the method for analyzing a component in a sample and the method for specific isolation of a component in a sample according to the present application. Samples of blood, etc., are easy to handle, and delivery to an analysis center, etc., also is simplified, by handling the sample together with a thermoplastic resin. Accordingly, bedside diagnosis becomes possible at medical institutions, university medical schools, and other research institutions, general hospitals, etc. Also, diagnoses of patients or analysis of samples in remote locations can be performed because samples at hospitals and various inspection agencies lacking mass spectrometers can be analyzed at an analysis center.

The invention claimed is:

1. A method for analyzing a component in a sample, the method including a step for irradiating a thermoplastic resin film internally containing the sample with ionizing laser light of a mass spectrometer.

2. The method of analysis of claim 1, wherein the thermoplastic resin film internally containing the sample is formed by:
   a step for heating and melting the thermoplastic resin; and
   a step for cooling the molten thermoplastic resin while causing the thermoplastic resin to make contact with the sample.

3. The method of analysis of claim 1, wherein the sample is a biological sample.

4. The method of analysis of claim 2, wherein the sample is a biological sample.

5. The method of analysis of claim 3, wherein the biological sample is blood.

6. The method of analysis of claim 4, wherein the biological sample is blood.

7. The method of analysis of claim 2, wherein the sample, before coming into contact with the molten thermoplastic resin, is dried.

8. The method of analysis of claim 2, wherein the sample, before coming into contact with the molten thermoplastic resin, is dried.

9. The method of analysis of claim 7, wherein the sample, before coming into contact with the molten thermoplastic resin, is in a thin film form.

10. The method of analysis of claim 8, wherein the sample, before coming into contact with the molten thermoplastic resin, is in a thin film form.

11. The method of analysis of claim 1, wherein the component in the sample analysed by the method of analysis is a peptide hormone or a lipid.

12. The method of analysis of claim 2, wherein the component in the sample analysed by the method of analysis is a peptide hormone or a lipid.

13. A method for specific isolation of a component in a sample, the method including a step for irradiating a thermoplastic resin film internally containing the sample with ionizing laser light of a mass spectrometer.

14. The method of specific isolation of claim 13, wherein the thermoplastic resin film internally containing the sample is formed by:
   a step for heating and melting the thermoplastic resin; and
   a step for cooling the molten thermoplastic resin while causing the thermoplastic resin to make contact with the sample.

15. The method of specific isolation of claim 13, wherein the sample is a biological sample.

16. The method of specific isolation of claim 15, wherein the biological sample is blood.

17. The method of specific isolation of claim 13, wherein the sample, before coming into contact with the molten thermoplastic resin, is dried.

18. The method of specific isolation of claim 17, wherein the sample, before coming into contact with the molten thermoplastic resin, is in a thin film form.

19. A sample for mass spectrometry, wherein the sample is contained in a thermoplastic resin film.

20. The sample for mass spectrometry of claim 19, wherein the sample is a biological sample.

* * * * *